US007989428B2

(12) United States Patent
Go et al.

(10) Patent No.: US 7,989,428 B2
(45) Date of Patent: Aug. 2, 2011

(54) COMBINED TELOMERASE INHIBITOR AND GEMCITABINE FOR THE TREATMENT OF CANCER

(75) Inventors: Ning F. Go, Palo Alto, CA (US); Robert J. Tressler, Capitola, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 12/446,931

(22) PCT Filed: Oct. 30, 2007

(86) PCT No.: PCT/US2007/022850

§ 371 (c)(1),
(2), (4) Date: Apr. 23, 2009

(87) PCT Pub. No.: WO2008/054711

PCT Pub. Date: May 8, 2008

(65) Prior Publication Data

US 2010/0016407 A1 Jan. 21, 2010

Related U.S. Application Data

(60) Provisional application No. 60/855,583, filed on Oct. 30, 2006.

(51) Int. Cl.
*A61K 48/00* (2006.01)
*C12N 15/11* (2006.01)

(52) U.S. Cl. .................................... 514/44 R; 514/44 A

(58) Field of Classification Search ................ 514/44 A, 514/44 R

See application file for complete search history.

(56) References Cited

U.S. PATENT DOCUMENTS

| | | | |
|---|---|---|---|
| 4,394,448 A | 7/1983 | Szoka, Jr. et al. | |
| 4,897,355 A | 1/1990 | Eppstein et al. | |
| 5,583,016 A | 12/1996 | Villeponteau et al. | |
| 5,629,154 A | 5/1997 | Kim et al. | |
| 5,891,639 A | 4/1999 | Harley et al. | |
| 5,952,490 A | 9/1999 | Hanecak et al. | |
| 6,261,836 B1 | 7/2001 | Cech et al. | |
| 6,331,399 B1 | 12/2001 | Monia et al. | |
| 6,444,650 B1 | 9/2002 | Cech et al. | |
| 6,548,298 B2 | 4/2003 | Villeponteau et al. | |
| 6,608,036 B1 * | 8/2003 | Gryaznov et al. | 514/44 A |

(Continued)

FOREIGN PATENT DOCUMENTS

WO WO-98/28442 7/1998

(Continued)

OTHER PUBLICATIONS

Asai, A. et al., "A Novel Telomerase Template Antagonist (GRN163) as a Potential Anticancer Agent," *Cancer Res. 63* (2003), pp. 3931-3939.

(Continued)

*Primary Examiner* — Jon E Angell
(74) *Attorney, Agent, or Firm* — Leslie A. Mooi

(57) ABSTRACT

A method and kit for inhibiting the proliferation of cancer cells are disclosed, based on a combination of a gemcitabine and a telomerase inhibitor. When used in cancer therapy, the two compounds in combination enhance the anti-cancer treatment efficacy obtained with gemcitabine alone or the telomerase inhibitor alone. Preferably, efficacy is supraadditive or synergistic in nature relative to the combined effects of the individual agents, with minimal exacerbation of side effects.

11 Claims, 1 Drawing Sheet

•No GRN163L single agent efficacy at 15 mg/kg.
•No gemcitabine single agent efficacy at 100 mg/kg qw.
•Combination of sub-efficacious doses GRN163L and gemcitabine shows synergistic effect.

U.S. PATENT DOCUMENTS

| | | | | |
|---|---|---|---|---|
| 6,995,145 | B1 | 2/2006 | Au et al. | |
| 7,067,497 | B2 | 6/2006 | Hanecak et al. | |
| 7,485,717 | B2 | 2/2009 | Gryaznov et al. | |
| 7,494,982 | B2 | 2/2009 | Gryaznov et al. | |
| 2006/0128651 | A1* | 6/2006 | Au et al. | 514/44 |
| 2007/0015723 | A1 | 1/2007 | Hanecak et al. | |
| 2007/0270363 | A1 | 11/2007 | Bennett et al. | |
| 2010/0010064 | A1 | 1/2010 | Moore et al. | |
| 2010/0104586 | A1 | 4/2010 | Tressler et al. | |

FOREIGN PATENT DOCUMENTS

| | | |
|---|---|---|
| WO | WO-2005/000245 | 1/2005 |
| WO | WO-2006/113426 | 10/2006 |
| WO | WO-2006/113470 | 10/2006 |
| WO | WO-2006/124904 | 11/2006 |
| WO | WO-2008/112129 | 9/2008 |

OTHER PUBLICATIONS

Blackburn, E., "Telomerases," *Annu. Rev. Biochem.* 61 (1992), pp. 113-129.

Chen, J. et al., "Secondary structure of vertebrate telomerase RNA," *Cell* 100 (2000), pp. 503-514.

Gryaznov, S. et al., "Oligonucleotide N3'->P5' thiophosphoramidate telomerase template antagonists as potential anticancer agents," *Nucleosides, Nucleotides & Nucl. Acids 22*(5-8) (2003), pp. 577-581.

Harley, C., "Telomere loss: Mitotic clock or genetic time bomb?" *Mutation. Res. 256* (1991), pp. 271-282.

Herbert, B-S. et al., "Oligonucleotide N3'->P5' phosphoramidates as efficient telomerase inhibitors," *Oncogene 21*(4) (2002), pp. 638-642.

Kim, M. et al., "A low threshold level of expression of mutant-template telomerase RNA inhibits human tumor cell proliferation," *Proc. Natl. Acad. Sci. USA 98*(14) (2001), pp. 7982-7987.

Kraemer, K. et al., "Chemosensitization of bladder cancer cell lines by human telomerase reverse transcriptase antisense treatment," *J. Urology 172*(5 Pt. 1) (2004), pp. 2023-2028.

Kupihar, Z. et al., "Synthesis and application of a novel, crystalline phosphoramidite monomer with thiol terminus, suitable for the synthesis of DNA conjugates," *Bioorg. Med. Chem. 9*(5) (2001), pp. 1241-1247.

Lebedeva, I. et al., "Antisense oligonucleotides: promise and reality," *Annu. Rev. Pharmacol. Toxicol. 41* (2001), pp. 403-419.

Macejak, D. et al., "Adenovirus-mediated expression of a ribozyme to c-myb mRNA inhibits smooth muscle cell proliferation and neointima formation in vivo," *J. Virol. 73*(9) (1999), pp. 7745-7751.

McCurdy, S. et al., "An Improved Method for the Synthesis of N3'->P5' Phosphoramidate Oligonucleotides," *Tetrahedron Lett. 38*(2) (1997), pp. 207-210.

Mishra, R. et al., "Improved leishmanicidal effect of phosphorotioate antisense oligonucleotides by LDL-mediated delivery," *Biochim. Biophys. Acta 1264*(2) (1995), pp. 229-237.

Nelson, J S. et al., "N3'-P5' oligodeoxyribonucleotide phosphoramidates: a new method of synthesis based on a phosphoramidate amine-exchange reaction," *J. Org. Chem. 62* (1997), pp. 7278-7287.

Pongracz, K. et al., "Oligonucleotide N3'—>P5' thiophosphoramidates: synthesis and properties," *Tetrahedron Lett. 40* (1999), pp. 7661-7664.

Pruzan, R. et al., "Allosteric inhibitors of telomerase: oligonucleotide N3'—>P5' phosporamidates," *Nucl. Acids Res. 30*(21 (2002), pp. 559-568.

Rump, E. et al., "Preparation of conjugates of oligodeoxynucleotides and lipid structures and their interaction with low-density lipoprotein," *Bioconjugate Chem. 9* (1998), pp. 341-349.

Shea, R. et al., "Synthesis, hybridization properties and antiviral activity of lipid-oligodeoxynucleotide conjugates," *Nucl. Acids Res. 18*(13) (1990), pp. 3777-3783.

Zeng, Y. et al., "MicroRNAs and small interfering RNAs can inhibit mRNA expression by similar mechanisms," *Proc. Natl. Acad. Sci. USA 100*(17) (2003), pp. 9779-9784.

PCT Search Report for PCT/US2007/022850, mailed Sep. 30, 2008, 1 page.

Supplementary European Search Report and European Search Opinion for Appl. No. EP 07867297.9, dated Oct. 11, 2011, 7 pages.

Go, N. et al., "Single agent and combination treatment studies with the telomerase inhibitor GRN163L in ovarian cancer and non-small cell lung carcinoma (NSCLC) xenograft models", *Eur. J. Cancer* 4(Suppl. 12) (2006), p. 189, Abstract.

Hochreiter, A. et al., "Telomerase template antagonist GRN163L disrupts telomere maintenance, tumor growth, and metastasis of breast cancer", *Clin. Cancer Res.* 12(10) (2006), pp. 3184-3192.

Senkal, C. et al., "Potent antitumor activity of a novel cationic pyridinium-ceramide alone or in combination with gemcitabine against human head and neck squamous cell carcinomas in vitro and in vivo", *J. Pharmacol. Exp. Ther.* 317(3) (2006), pp. 1188-1199.

Univ. Liverpool Clinical Trial, "A prospective, phase III, controlled, multicentre, randomised clinical trial comparing combination gemcitabine and capecitabine therapy with concurrent and sequential chemoimmunotherapy using a telomerase vaccine in locally advanced and metastatic pancreatic cancer" *ISRCTN43482138* (2005) 3 pages.

* cited by examiner

SEQUENCE LISTING

<160> NUMBER OF SEQ ID NOS: 27

<210> SEQ ID NO 1
<211> LENGTH: 554
<212> TYPE: RNA
<213> ORGANISM: Homo sapiens

<400> SEQUENCE: 1
ggguugcgga gggugggccu gggaggggug guggccauuu uuugucuaac ccuaacugag 60
aagggcguag gcgccgugcu uuugcucccc gcgcgcuguu uuucucgcug acuuucagcg 120
ggcggaaaag ccucggccug ccgccuucca ccguucauuc uagagcaaac aaaaaauguc 180
agcugcuggc ccguucgccu cccggggacc ugcggcgggu cgccugccca gcccccgaac 240
cccgccugga gccgcggucg gcccggggcu ucuccggagg cacccacugc caccgcgaag 300
aguugggcuc ugucagccgc gggucucucg ggggcgaggg cgagguucac cguuucaggc 360
cgcaggaaga ggaacggagc gagucccgcc gcggcgcgau ucccugagcu gugggacgug 420
cacccaggac ucggcucaca caugcaguuc gcuuuccugu uggugggggg aacgccgauc 480
gugcgcaucc gucaccccuc gccggcagug ggggcuugug aacccccaaa ccugacugac 540
ugggccagug ugcu 554

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2 acatttttttg tttgctctag 20

<210> SEQ ID NO 3

-continued

<211> LENGTH: 30
<212> TYPE: DNA
<213> ORGANISM: Artificial Sequence
<220> FEATURE:
<223> OTHER INFORMATION: Oligonucleotide

<400> SEQUENCE: 3
gctctagaat gaacggtgga aggcggcagg 30

<210> SEQ ID NO 4
<211> LENGTH: 14
<212> TYPE: DNA
<213> ORGANISM: Artificial Sequence
<220> FEATURE:
<223> OTHER INFORMATION: Oligonucleotide

<400> SEQUENCE: 4
gtggaggcgg cagg 14

<210> SEQ ID NO 5
<211> LENGTH: 13
<212> TYPE: DNA
<213> ORGANISM: Artificial Sequence
<220> FEATURE:
<223> OTHER INFORMATION: Oligonucleotide

<400> SEQUENCE: 5
ggaaggcggc agg 13

<210> SEQ ID NO 6
<211> LENGTH: 13
<212> TYPE: DNA
<213> ORGANISM: Artificial Sequence
<220> FEATURE:
<223> OTHER INFORMATION: Oligonucleotide

<400> SEQUENCE: 6
gtggaaggcg gca 13

<210> SEQ ID NO 7
<211> LENGTH: 11
<212> TYPE: DNA
<213> ORGANISM: Artificial Sequence
<220> FEATURE:
<223> OTHER INFORMATION: Oligonucleotide

<400> SEQUENCE: 7
gtggaaggcg g 11

<210> SEQ ID NO 8
<211> LENGTH: 13
<212> TYPE: DNA
<213> ORGANISM: Artificial Sequence
<220> FEATURE:
<223> OTHER INFORMATION: Oligonucleotide

<400> SEQUENCE: 8
cggtggaagg cgg 13

<210> SEQ ID NO 9
<211> LENGTH: 13
<212> TYPE: DNA
<213> ORGANISM: Artificial Sequence
<220> FEATURE:
<223> OTHER INFORMATION: Oligonucleotide

<400> SEQUENCE: 9
acggtggaag gcg 13

<210> SEQ ID NO 10
<211> LENGTH: 16
<212> TYPE: DNA
<213> ORGANISM: Artificial Sequence
<220> FEATURE:
<223> OTHER INFORMATION: Oligonucleotide

<400> SEQUENCE: 10
aacggtggaa ggcggc 16

<210> SEQ ID NO 11
<211> LENGTH: 18
<212> TYPE: DNA
<213> ORGANISM: Artificial Sequence
<220> FEATURE:
<223> OTHER INFORMATION: Oligonucleotide

<400> SEQUENCE: 11
atgaacggtg gaaggcgg 18

<210> SEQ ID NO 12
<211> LENGTH: 13
<212> TYPE: DNA
<213> ORGANISM: Artificial Sequence
<220> FEATURE:
<223> OTHER INFORMATION: Oligonucleotide

<400> SEQUENCE: 12
tagggttaga caa 13

<210> SEQ ID NO 13
<211> LENGTH: 13
<212> TYPE: DNA
<213> ORGANISM: Artificial Sequence
<220> FEATURE:
<223> OTHER INFORMATION: Oligonucleotide

<400> SEQUENCE: 13
cagttagggt tag 13

<210> SEQ ID NO 14
<211> LENGTH: 12
<212> TYPE: DNA
<213> ORGANISM: Artificial Sequence
<220> FEATURE:
<223> OTHER INFORMATION: Oligonucleotide

<400> SEQUENCE: 14
tagggttaga ca 12

<210> SEQ ID NO 15
<211> LENGTH: 11
<212> TYPE: DNA
<213> ORGANISM: Artificial Sequence
<220> FEATURE:
<223> OTHER INFORMATION: Oligonucleotide

<400> SEQUENCE: 15
tagggttaga c 11

<210> SEQ ID NO 16
<211> LENGTH: 11
<212> TYPE: DNA
<213> ORGANISM: Artificial Sequence
<220> FEATURE:

<223> OTHER INFORMATION: Oligonucleotide

<400> SEQUENCE: 16
gttagggtta g 11

<210> SEQ ID NO 17
<211> LENGTH: 13
<212> TYPE: DNA
<213> ORGANISM: Artificial Sequence
<220> FEATURE:
<223> OTHER INFORMATION: Oligonucleotide

<400> SEQUENCE: 17
gttagggtta gac 13

<210> SEQ ID NO 18
<211> LENGTH: 15
<212> TYPE: DNA
<213> ORGANISM: Artificial Sequence
<220> FEATURE:
<223> OTHER INFORMATION: Oligonucleotide

<400> SEQUENCE: 18
gttagggtta gacaa 15

<210> SEQ ID NO 19
<211> LENGTH: 9
<212> TYPE: DNA
<213> ORGANISM: Artificial Sequence
<220> FEATURE:
<223> OTHER INFORMATION: Oligonucleotide

<400> SEQUENCE: 19 gggttagac 9

<210> SEQ ID NO 20
<211> LENGTH: 9
<212> TYPE: DNA
<213> ORGANISM: Artificial Sequence
<220> FEATURE:
<223> OTHER INFORMATION: Oligonucleotide

<400> SEQUENCE: 20 cagttaggg 9

<210> SEQ ID NO 21
<211> LENGTH: 12
<212> TYPE: DNA
<213> ORGANISM: Artificial Sequence
<220> FEATURE:
<223> OTHER INFORMATION: Oligonucleotide

<400> SEQUENCE: 21
cccttctcag tt 12

<210> SEQ ID NO 22
<211> LENGTH: 12
<212> TYPE: DNA
<213> ORGANISM: Artificial Sequence
<220> FEATURE:
<223> OTHER INFORMATION: Oligonucleotide

<400> SEQUENCE: 22
cgcccttctc ag 12

<210> SEQ ID NO 23

-continued

```
<211> LENGTH: 13
<212> TYPE: DNA
<213> ORGANISM: Artificial Sequence
<220> FEATURE:
<223> OTHER INFORMATION: Oligonucleotide

<400> SEQUENCE: 23

taggtgtaag caa                                                13


<210> SEQ ID NO 24
<211> LENGTH: 13
<212> TYPE: DNA
<213> ORGANISM: Artificial Sequence
<220> FEATURE:
<223> OTHER INFORMATION: Oligonucleotide

<400> SEQUENCE: 24

ttgtctaacc cta                                                13


<210> SEQ ID NO 25
<211> LENGTH: 11
<212> TYPE: DNA
<213> ORGANISM: Artificial Sequence
<220> FEATURE:
<223> OTHER INFORMATION: Oligonucleotide

<400> SEQUENCE: 25

gttgagtgta g                                                  11


<210> SEQ ID NO 26
<211> LENGTH: 6
<212> TYPE: DNA
<213> ORGANISM: Artificial Sequence
<220> FEATURE:
<223> OTHER INFORMATION: Oligonucleotide

<400> SEQUENCE: 26

ttaggg                                                         6


<210> SEQ ID NO 27
<211> LENGTH: 10
<212> TYPE: DNA
<213> ORGANISM: Artificial Sequence
<220> FEATURE:
<223> OTHER INFORMATION: Oligonucleotide

<400> SEQUENCE: 27

tttttttttt                                                    10
```

COMBINED TELOMERASE INHIBITOR AND GEMCITABINE FOR THE TREATMENT OF CANCER

FIELD OF THE INVENTION

The invention is directed to anticancer treatment, and in particular to inhibition of tumor growth or cancer-cell proliferation, by treatment with a telomerase inhibitor in combination with gemcitabine.

BACKGROUND

Although many cancers can be cured by surgical resection, chemotherapy is often used as an adjunct to surgical therapy, and it is widely used in the treatment of inoperable or metastatic malignancy. In view of the continuing high number of deaths each year resulting from cancer, a continuing need exists to identify effective and relatively nontoxic therapeutic regimens for use in anticancer treatment.

Many effective chemotherapeutic agents have been identified over the past few decades, and these are generally grouped into several categories on the basis of their mechanism of action. Combined-therapy treatments have become more common, in view of the perceived advantage of attacking the disease via multiple avenues. In practice, however, many such combinations do not provide even simple additivity of therapeutic effects.

Ideally, a combined-drug approach for cancer treatment should provide a significant boost in efficacy and/or a significant reduction in undesired side effects, due to a reduced dose of the more toxic component and/or a reduction in the development of drug-resistance in the cancer being treated. Particularly desirable are combination therapies which produce therapeutic results that are supraadditive or synergistic in nature relative to the effects of the individual agents, with minimal exacerbation of side effects.

SUMMARY

In one aspect, the invention includes a method for inhibiting the proliferation of cancer cells, by the steps of: (a) exposing the cells to gemcitabine, and (b) either proceeding, following, or concomitantly with step (a), exposing the cells to an oligonucleotide telomerase inhibitor of the type composed of an oligonucleotide having nuclease-resistant intersubunit linkages and an oligonucleotide sequence effective to bind by sequence-specific hybridization to a template region of hTR.

The internucleoside linkages in the oligonucleotide may be selected from N3'→P5' phosphoramidate and N3'→P5' thiophosphoramidate linkages. The telomerase inhibitor may include a lipid moiety (i) selected from the group consisting of fatty acids, sterols, and derivatives thereof, and (ii) attached covalently to one end of the oligonucleotide. The oligonucleotide may be 10-20 bases in length. An exemplary oligonucleotide telomerase inhibitor is characterized by:

(i) N3'→P5' thiophosphoramidate internucleoside linkages;

(ii) having the sequence identified as SEQ ID NO: 12; and (iii) a palmitoyl (C16) moiety linked to the 5' terminus of the oligonucleotide via a glycerol or aminoglycerol linker.

The exemplary compound may be that designated herein as GRN163L, where step (b) of the method may include infusing the telomerase inhibitor intravenously to the subject under infusion conditions effective to produce a blood concentration of the inhibitor of between 1 nM and 100 μM.

Each exposing step (a) and (b) may include administering gemcitabine and the telomerase inhibitor to the subject in an amount effective, when each agent is administered alone, to inhibit proliferation of cancer cells in the subject.

The telomerase inhibitor and gemcitabine may be administered to a subject diagnosed with a cancer selected from the group consisting of non-small cell lung cancer, pancreatic cancer, breast cancer, oesophageal cancer, and lymphomas, bladder cancer, cancer of the lymph system, epithelial ovarian cancer, cancer of the bile ducts, cancer of the gallbladder, and germ cell tumors The method may provide a supraadditive inhibiting effect relative to the effects of the individual gemcitabine and the telomerase inhibitor agents.

In another aspect, the invention includes enhancing the anti-cancer treatment efficacy of gemcitabine administered to a subject, by administering to the subject, before, during, or after administering gemcitabine, an oligonucleotide telomerase inhibitor of the type composed of an oligonucleotide having nuclease-resistant intersubunit linkages and an oligonucleotide sequence effective to bind by sequence-specific hybridization to a template region of hTR. Exemplary telomerase inhibitors are as above.

The telomerase inhibitor may be administered in an amount effective to inhibit the proliferation of cancer cells in the subject, when the telomerase inhibitor is administered alone. The enhanced treatment efficacy may be evidenced by an increased survival time of the subject, an inhibition of tumor growth in the subject, or a combination thereof. The telomerase inhibitor and gemcitabine may be administered to the subject as a composition containing both inhibitors.

Also disclosed is a kit for use in cancer therapy, comprising (a) a dose of gemcitabine in an amount effective, when administered alone, to inhibit the proliferation of cancer cells in a subject, and (b) a dose of an oligonucleotide telomerase inhibitor of the type composed of an oligonucleotide having nuclease-resistant intersubunit linkages and an oligonucleotide sequence effective to bind by sequence-specific hybridization to a template region of hTR, in amount effective, when administered alone, to inhibit proliferation of cancer cells in the subject. Exemplary telomerase inhibitors are as above.

In still other aspects, the invention includes the use of a gemcitabine and an oligonucleotide telomerase inhibitor in the manufacture of a medicament for treating cancer in a subject, and the use of an oligonucleotide telomerase inhibitor in the manufacture of a medicament for treating cancer in a subject who is being treated with a gemcitabine, for the purpose of enhancing the anti-cancer efficacy of gemcitabine in the subject.

These and other objects and features of the invention will become more fully apparent when the following detailed description of the invention is read in conjunction with the accompanying drawings.

DETAILED DESCRIPTION OF THE INVENTION

I. Definitions

Figure 1:
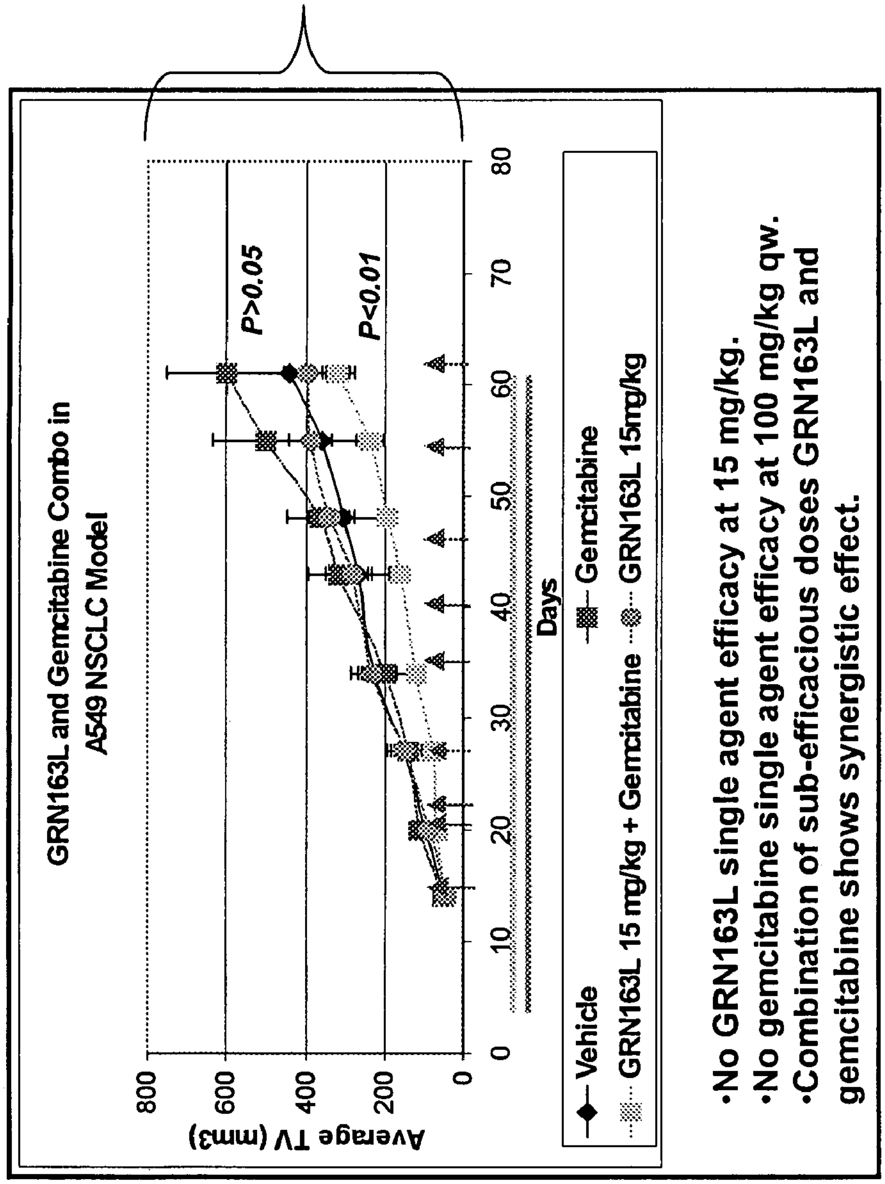
FIG. 1 is a plot of average tumor volume (TV) as of A549 tumor cells injected subcutaneously in mice after treatment, over a 60 day period, with vehicle alone (dark diamonds), gemcitabine alone (dark squares), GRN163L alone (circles) and a combination of GRNL 163L plus gemcitabine (light squares).

The terms below have the following meanings unless indicated otherwise.

A "polynucleotide" or "oligonucleotide" refers to a ribose and/or deoxyribose nucleoside subunit polymer or oligomer having between about 2 and about 200 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3'→P5' thiophosphoramidate, and phosphorothioate linkages. The term also includes such polymers or oligomers having modifications, known to one skilled in the art, to the sugar (e.g., 2' substitutions), the base (see the definition of "nucleoside" below), and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

The term "nucleoside" includes the natural nucleosides, including 2'-deoxy and 2'-hydroxyl forms, e.g., as described in Komberg and Baker, DNA Replication, 2nd Ed. (Freeman, San Francisco, 1992), and analogs. "Analogs", in reference to nucleosides, includes synthetic nucleosides having modified nucleobase moieties (see definition of "nucleobase" below) and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman (*Chemical Reviews* 90:543-584, 1990). An oligonucleotide containing such nucleosides, and which typically contains synthetic nuclease-resistant internucleoside linkages, may itself be referred to as an "analog".

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

The term "lipid" is used broadly herein to encompass substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. Preferred lipids are fatty acids and their derivatives, hydrocarbons and their derivatives, and sterols, such as cholesterol.

Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters.

The term "hydrocarbon" encompasses compounds that consist only of hydrogen and carbon, joined by covalent bonds. The term encompasses open chain (aliphatic) hydrocarbons, including straight chain and branched hydrocarbons, and saturated as well as mono-and poly-unsaturated hydrocarbons. The term also encompasses hydrocarbons containing one or more aromatic rings.

As used herein, the term "lipid" also includes amphipathic compounds containing both lipid and hydrophilic moieties.

The term "substituted" refers to a compound which has been modified by the exchange of one atom or moiety for another, typically substitution of hydrogen by a different atom or moiety. In particular, the term is used in reference to halogenated hydrocarbons and fatty acids, particularly those in which one or more hydrogen atoms are substituted with fluorine.

An "oligonucleotide telomerase inhibitor" refers to a telomerase inhibitor composed of an oligonucleotide having nuclease-resistant intersubunit linkages and an oligonucleotide sequence effective to bind by sequence-specific hybridization to a template region of the RNA component of human telomerase. An "hTR template inhibitor" is an oligonucleotide telomerase inhibitor that blocks the template region (the region spanning nucleotides 30-67 of SEQ ID NO: 1 herein) of the RNA component of human telomerase, thereby inhibiting the activity of the enzyme. The inhibitor is typically an oligonucleotide that is able to hybridize to this region. Preferably, the oligonucleotide includes a sequence effective to hybridize to a more specific portion of this region, having sequence 5'-CUAACCCUAAC-3' (SEQ ID NO: 12), spanning nucleotides 46-56 of SEQ ID NO: 1 herein.

A compound is said to "inhibit the proliferation of cancer cells" if the proliferation of cells in the presence of the compound is less than that observed in the absence of the compound. That is, proliferation of the cells is either slowed or halted in the presence of the compound. Inhibition of cancer-cell proliferation may be evidenced, for example, by reduction in the number of cells or rate of expansion of cells, reduction in tumor mass or the rate of tumor growth, or increase in survival rate of a subject being treated.

Administration of a telomerase inhibitor to a subject is effective to "enhance the anti-cancer treatment efficacy of a gemcitabine" if the subject shows a reduced rate of tumor growth and/or an enhanced survival rate with combined therapy over therapy with gemcitabine alone.

An oligonucleotide having "nuclease-resistant linkages" refers to one whose backbone has subunit linkages that are substantially resistant to nuclease cleavage, in non-hybridized or hybridized form, by common extracellular and intracellular nucleases in the body; that is, the oligonucleotide shows little or no nuclease cleavage under normal nuclease conditions in the body to which the oligonucleotide is exposed. The N3'→P5' phosphoramidate (NP) or N3'→P5' thiophosphoramidate (NPS) linkages described below are nuclease resistant.

II. Treatment of Cancer with a Gemcitabine

"Gemcitabine" in Gemcitabine HCl form, is 2'-deoxy-2',2'-difluorocytidine monohydrochloride ((beta)-isomer). The structural formula is as follows:

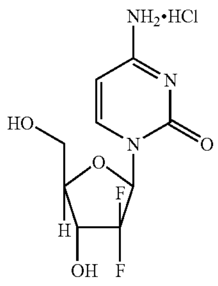

The clinical formulation is supplied in a sterile form for intravenous use. Gemcitabine is sold under the trade name Gemzar™, and vials of Gemzar™ contain either 200 mg or 1 g of gemcitabine HCl (expressed as free base) formulated with mannitol (200 mg or 1 g, respectively) and sodium acetate (12.5 mg or 62.5 mg, respectively) as a sterile lyophilized powder. Hydrochloric acid and/or sodium hydroxide may be added for pH adjustment. The term "gemcitabine, as used herein, includes pharmaceutically active salts and acids of the compound, as well as gemcitabine prodrugs that can be converted to gemcitabine in vivo.

It is widely accepted that gemcitabine acts by replacing one of the building blocks of nucleic acids, in this case cytidine, during DNA replication. The process arrests tumor growth, as new nucleosides cannot be attached to the "faulty" nucleoside, resulting in apoptosis (cellular "suicide"). Recent evidence indicates that gemcitabine may interfere with excision repair cross-complementing 1 (ERCC1) nucleotide excision repair activity.

Gemcitabine is used in various carcinomas: non-small cell lung cancer, pancreatic cancer, and breast cancer, and has showed experimental or clinical promise for oesophageal cancer, lymphomas and various other tumor types, such as consisting of bladder cancer, cancer of the lymph system, epithelial ovarian cancer, cancer of the bile ducts, cancer of the gallbladder, and germ cell tumors of the ovaries and testes. For use in the treatment of cancer in combination with an oligonucleotide telomerase inhibitor, in accordance with the present invention, gemcitabine may be administered at doses recommended in the product insert. However, one advantage of the present invention is that gemcitabine, when administered in combination with the telomerase inhibitor, may be administered at does lower than single-agent doses, thus reducing side effects and the overall toxicity of the compound, while achieving comparable or superior anti-cancer treatment effects.

III. Treatment of Cancer with a Telomerase Inhibitor

Telomerase is a ribonucleoprotein that catalyzes the addition of telomeric repeat sequences (having the sequence 5'-TTAGGG-3' in humans) to chromosome ends. See e.g. Blackburn, 1992, *Ann. Rev. Biochem.* 61:113-129. The enzyme is expressed in most cancer cells but not in mature somatic cells. Loss of telomeric DNA may play a role in triggering cellular senescence; see Harley, 1991, *Mutation Research* 256:271-282. A variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma). Targeting of telomerase can be effective in providing treatments that discriminate between malignant and normal cells to a high degree, avoiding many of the deleterious side effects that can accompany chemotherapeutic regimens which target dividing cells indiscriminately.

Inhibitors of telomerase identified to date include oligonucleotides, preferably oligonucleotides having nuclease resistant linkages, as well as small molecule compounds.

Oligonucleotide-Based Telomerase Inhibitors: Sequence and Composition

The genes encoding both the protein and RNA components of human telomerase have been cloned and sequenced (see U.S. Pat. Nos. 6,261,836 and 5,583,016, respectively, both of which are incorporated herein by reference). Oligonucleotides can be targeted against the mRNA encoding the telomerase protein component (the human form of which is known as human telomerase reverse transcriptase, or hTERT) or the RNA component of the telomerase holoenzyme (the human form of which is known as human telomerase RNA, or hTR).

The nucleotide sequence of the RNA component of human telomerase (hTR) is shown in the Sequence Listing below (SEQ ID NO: 1), in the 5'→3' direction. The sequence is shown using the standard abbreviations for ribonucleotides; those of skill in the art will recognize that the sequence also represents the sequence of the cDNA, in which the ribonucleotides are replaced by deoxyribonucleotides, with uridine (U) being replaced by thymidine (T). The template sequence of the RNA component is located within the region defined by nucleotides 46-56 (5'-CUAACCCUAAC-3'), which is complementary to a telomeric sequence composed of about one-and-two-thirds telomeric repeat units. The template region functions to specify the sequence of the telomeric repeats that telomerase adds to the chromosome ends and is essential to the activity of the telomerase enzyme (see e.g. Chen et al., *Cell* 100:503-514, 2000; Kim et al., *Proc. Natl. Acad. Sci. USA* 98(14):7982-7987, 2001). The design of antisense, ribozyme or small interfering RNA (siRNA) agents to inhibit or cause the destruction of mRNAs is well known (see, for example, Lebedeva et al. Annual Review of Pharmacology and Toxicology, Vol. 41: 403-419, April 2001; Macejak, D. et al., Journal of Virology, Vol. 73 (9): p. 7745-7751, September 1999, and Zeng, Y. et al., PNAS Vol. 100(17) pp. 9779-9784, Aug. 19, 2003), and such agents may be designed to target the hTERT mRNA and thereby inhibit production of hTERT protein in a target cell, such as a cancer cell (see, for example, U.S. Pat. Nos. 6,444,650 and 6,331,399).

Oligonucleotides targeting hTR (that is, the RNA component of the enzyme) act as inhibitors of telomerase enzyme activity by blocking or otherwise interfering with the interaction of hTR with the hTERT protein, which interaction is necessary for telomerase function. See, for example, Villeponteau et al., U.S. Pat. No. 6,548,298.

A preferred target region of hTR is the template region, spanning nucleotides 30-67 of SEQ ID NO:1. Oligonucleotides targeting this region are referred to herein as "hTR template inhibitors" (see e.g. Herbert et al., *Oncogene* 21(4): 638-42 (2002).) Preferably, such an oligonucleotide includes a sequence which is complementary or near-complementary to some portion of the 11-nucleotide region having sequence 5'-CUAACCCUAAC-3', spanning nucleotides 46-56 of SEQ ID NO: 12.

Another preferred target region is the region spanning nucleotides 137-179 of hTR (see Pruzan et al., *Nucl. Acids Research,* 30:559-568, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR. Preferred hTR targeting sequence are given below, and identified by SEQ ID NOS: 2-22.

The region of the therapeutic oligonucleotide that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide is thus selected to include a sequence of at least 5 nucleotides exactly complementary to the hTR target, and enhanced telomerase inhibition may be obtained if increasing lengths of complementary sequence are employed, such as at least 8, at least 10, at least 12, at least 13 or at least 15 nucleotides exactly complementary to the hTR target. In other embodiments, the sequence of the oligonucleotide includes a sequence of from at least 5 to 20, from at least 8 to 20, from at least 10 to 20 or from at least 10 to 15 nucleotides exactly complementary to the hTR target sequence.

Optimal telomerase inhibitory activity may be obtained when the full length of the oligonucleotide is selected to be complementary to the hTR target sequence. However, it is not necessary that the full length of the oligonucleotide is exactly complementary to the target sequence, and the oligonucleotide sequence may include regions that are not complementary to the target sequence. Such regions may be added, for example, to confer other properties on the compound, such as sequences that facilitate purification. Alternatively, an oligonucleotide may include multiple repeats of a sequence complementary to an hTR target sequence.

If the oligonucleotide is to include regions that are not complementary to the target sequence, such regions are typically positioned at one or both of the 5' or 3' termini. Exemplary sequences targeting human telomerase RNA (hTR) include the following:

| hTR Targeting Sequence | Region of SEQ ID NO: 1 | SEQ ID NO: |
|---|---|---|
| ACATTTTTTGTTTGCTCTAG | 160-179 | 2 |
| GCTCTAGAATGAACGGTGGAAGGCGGCAGG | 137-166 | 3 |
| GTGGAGGCGGCAGG | 137-151 | 4 |
| GGAAGGCGGCAGG | 137-149 | 5 |
| GTGGAAGGCGGCA | 139-151 | 6 |
| GTGGAAGGCGG | 141-151 | 7 |
| CGGTGGAAGGCGG | 141-153 | 8 |
| ACGGTGGAAGGCG | 142-154 | 9 |
| AACGGTGGAAGGCGGC | 143-155 | 10 |
| ATGAACGGTGGAAGGCGG | 144-158 | 11 |
| TAGGGTTAGACAA | 42-54 | 12 |
| CAGTTAGGGTTAG | 46-58 | 13 |
| TAGGGTTAGACA | 42-53 | 14 |
| TAGGGTTAGAC | 42-52 | 15 |
| GTTAGGGTTAG | 46-56 | 16 |
| GTTAGGGTTAGAC | 44-56 | 17 |
| GTTAGGGTTAGACAA | 42-56 | 18 |
| GGGTTAGAC | 44-52 | 19 |
| CAGTTAGGG | 50-58 | 20 |
| CCCTTCTCAGTT | 54-65 | 21 |
| CGCCCTTCTCAG | 56-67 | 22 |

The internucleoside linkages in the oligonucleotide may include any of the available oligonucleotide chemistries, e.g. phosphodiester, phosphotriester, methylphosphonate, P3'→N5' phosphoramidate, N3'→P5' phosphoramidate, N3'→P5' thiophosphoramidate, and phosphorothioate. Typically, but not necessarily, all of the internucleoside linkages within the oligonucleotide will be of the same type, although the oligonucleotide component may be synthesized using a mixture of different linkages.

In preferred embodiments, the oligonucleotide has at least one N3'→P5' phosphoramidate (NP) or N3'→P5' thiophosphoramidate (NPS) linkage, which linkage may be represented by the structure: 3'-(—NH—P(═O)(—XR)—O—)-5', wherein X is O or S and R is selected from the group consisting of hydrogen, alkyl, and aryl; and pharmaceutically acceptable salts thereof, when XR is OH or SH. More preferably, the oligonucleotide includes all NP or, most preferably, all NPS linkages.

A particularly preferred sequence for an hTR template inhibitor oligonucleotide is the sequence complementary to nucleotides 42-54 of SEQ ID NO: 12 above. The oligonucleotide having this sequence (TAGGGTTAGACA) and N3'→P5' thiophosphoramidate (NPS) linkages is designated herein as GRN163. See, for example, Asai et al., *Cancer Research* 63:3931-3939(2003); Gryaznov et al., *Nucleosides Nucleotides Nucleic Acids* 22(5-8):577-81 (2003).

As shown in Table 1 below, this oligonucleotide (first row of table) inhibits telomerase at low concentrations in a biochemical assay (FlashPlate™; see Experimental Section). An alternative 13-mer, having the sequence CAGTTAGGGTTAG, complementary to nucleotides 46-58 of SEQ ID NO: 1 (fifth row of table), showed near-equivalent activity in the FlashPlate™ assay. The corresponding NP-linked oligonucleotide, and shorter (11- and 12-mer) oligonucleotides targeting the same region (complementary to nucleotides 42-53 and 42-42, respectively, of SEQ ID NO: 1), showed moderate activity. The effect is clearly sequence-specific, as shown by the mismatch and non-targeting sequences in the table.

The oligonucleotide GRN163 administered alone has shown inhibitory activity in vitro in cell culture, including epidermoid carcinoma, breast epithelium, renal carcinoma, renal adenocarcinoma, pancreatic, brain, colon, prostate, leukemia, lymphoma, myeloma, epidermal, cervical, ovarian and liver cancer cells.

The oligonucleotide GRN163 has also been tested and shown to be therapeutically effective in a variety of animal tumor models, including ovarian and lung, both small cell and non-small cell.

TABLE 1

Inhibition of Telomerase by NPS Oligonucleotides: Biochemical (FlashPlate) Assay

| Sequence, 5' to 3' | Description | $IC_{50}$, nM |
|---|---|---|
| TAGGGTTAGACAA SEQ ID NO: 12 | 13-mer (GRN163) | 0.045 ± 0.007 |
| TAGGTGTAAGCAA (SEQ ID NO: 23) | Mismatch of GRN163 sequence | 80 ± 31 |
| TTGTCTAACCCTA (SEQ ID NO: 24) | Complement of GRN163 sequence | 1000 ± 46 |
| TAGGGTTAGACAA ATCCCAATCTGTT | Duplex of GRN163 sequence | 8.9 ± 3.0 |
| CAGTTAGGGTTAG (SEQ ID NO: 13) | Alternative targeting 13-mer | 0.049 ± 0.007 |
| TAGGGTTAGACA (SEQ ID NO: 14) | 12-mer; truncation of GRN163 sequence | 0.36 ± 0.2 |
| TAGGGTTAGAC (SEQ ID NO: 15) | 11-mer; truncation of GRN163 sequence | 0.85 ± 0.35 |
| GTTAGGGTTAG (SEQ ID NO: 16) | Alternative targeting 11-mer | 0.51 ± 0.13 |
| GTTGAGTGTAG (SEQ ID NO: 25) | Mismatch of alternative targeting 11-mer | 177 ± 93 |

TABLE 1-continued

| Inhibition of Telomerase by NPS Oligonucleotides: Biochemical (FlashPlate) Assay | | |
|---|---|---|
| Sequence, 5' to 3' | Description | $IC_{50}$, nM |
| TAGGGTTAGACAA (SEQ ID NO; 12) | 13-mer (GRN163 sequence) with NP backbone | 0.7 ± 0.1 |
| TAGGTGTAAGCAA (SEQ ID NO: 2) | Mismatch of GRN163 sequence with NP backbone | >1000 |
| TTAGGG (SEQ ID NO: 26) | Telomere repeat unit | >1000 |
| TTTTTTTTTT (SEQ ID NO: 27) | Oligo-T 10-mer | >1000 |

C. Lipid-Oligonucleotide Conjugates

Preferably, the oligonucleotide-based enzyme inhibitor includes at least one covalently linked lipid group (see US Pubn. No. 2005/0113325, which is incorporated herein by reference). This modification provides superior cellular uptake properties, such that an equivalent biological effect may be obtained using smaller amounts of the conjugated oligonucleotide compared to the unmodified form. When applied to the human therapeutic setting, this may translate to reduced toxicity risks, and cost savings.

The lipid group L is typically an aliphatic hydrocarbon or fatty acid, including derivatives of hydrocarbons and fatty acids, with examples being saturated straight chain compounds having 14-20 carbons, such as myristic (tetradecanoic) acid, palmitic (hexadecanoic) acid, and stearic (octadeacanoic) acid, and their corresponding aliphatic hydrocarbon forms, tetradecane, hexadecane and octadecane. Examples of other suitable lipid groups that may be employed are sterols, such as cholesterol, and substituted fatty acids and hydrocarbons, particularly polyfluorinated forms of these groups. The scope of the lipid group L includes derivatives such as amine, amide, ester and carbamate derivatives. The type of derivative is often determined by the mode of linkage to the oligonucleotide, as exemplified below.

In one exemplary structure, the lipid moiety is palmitoyl amide (derived from palmitic acid), conjugated through an aminoglycerol linker to the 5' thiophosphate group of an NPS-linked oligonucleotide. The NPS oligonucleotide having the sequence shown for GRN163 and conjugated in this manner (as shown below) is designated GRN163L herein. In a second exemplary structure, the lipid, as a palmitoyl amide, is conjugated through the terminal 3' amino group of an NPS oligonucleotide.

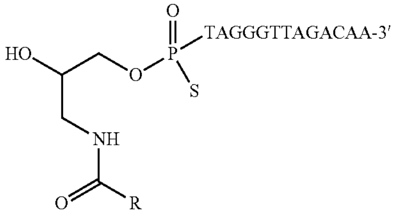

GRN163L

R = $-(CH_2)_{13}CH_3$ (palmitoyl)

As shown in Table 2, conjugation of a single fatty acid-type lipid significantly increased telomerase inhibitory activity in cell systems relative to the unconjugated oligonucleotide.

TABLE 2

| Inhibition of Telomerase by Lipid-Conjugated NPS Oligonucleotides (based on GRN163) | | |
|---|---|---|
| Lipid Substitution | Tm (° C.) of duplex with RNA | $IC_{50}$ in vitro, HT-3 cells, nM |
| none (GRN163) | 70.0 | 1600 |
| 3'-palmitic (GRN163L) | 66.5 | 160 |
| 3'-stearic | 67.1 | 140 |
| 3'-(bis)stearic | ~40 | 1960 |
| 3'-oleic | 66.8 | 930 |
| NH-$C_{16}$ (palmitoyl) on $3^{rd}$ 5' residue (G) | 62.6 | 500 |
| 5'-palmitic | 65.5 | 112 |
| 3'-palmitic-5'-palmitic | 61.3 | ~10000 |
| 3'-trityl | 66.1 | 3000 |

The effect of lipid conjugation on pharmacokinetics is illustrated by the data shown in Table 3, below, for a 4 mg/kg dose administered in rats. Target organ concentrations 6 hours after administration were also more favorable for GRN163L, with approx. 4-5 μM found in liver, kidney, and fat tissue, 2-3 μM in bone marrow and spleen, and about 0.5 μM in lymph node. Distribution of the unlipidated oligonucleotide, GRN163, was primarily to the kidney (about 18 μM), with only 1 μM or less in the remaining organ tissues noted above.

Table 4 presents further data directed to telomerase inhibition in vitro by GRN163 (unconjugated) and GRN163L (lipidated) in various cancer cell lines.

TABLE 3

| Comparative Pharmacokinetics of Lipidated (GRN163L) and Unlipidated (GRN163) NPS Oligonucleotide (Rat, 4 mg/kg dose) | | |
|---|---|---|
| | GRN163 | GRN163L |
| $T_{1/2}\alpha$, min | 17 | 20 |
| $T_{1/2}\beta$, hrs | 65-86 | 68-72 |
| $AUC_{0-\infty}$, μg-hr/g | 27 | 120 |
| $C_{max}$, μg/ml | 16 | 58 |
| % excreted in 24 h | 45 | 13 |

TABLE 4

| Comparative Telomerase Inhibitory Activity of Lipidated (GRN163L) and Unlipidated (GRN163) NPS Oligonucleotide in vitro | | |
|---|---|---|
| Cell Line | GRN163 $IC_{50}$ (μM) | GRN163L $IC_{50}$ (μM) |
| HT-3 (Cervical) | 1.62 | 0.3 |
| U251 (Glioblastoma) | 1.75 | 0.17 |
| U87 (Glioblastoma) | 0.75 | 0.11 |
| Hep3B (Hepatoma) | 6.5 | 0.36 |
| HepG2 (Hepatoma) | 2.72 | 0.48 |
| NCI-H522 (Lung) | 2.59 | 0.23 |
| RPMI 8226 (Myeloma) | 2.67 | 0.38 |
| Ovcar5 (Ovarian) | 3.74 | 0.92 |
| DU 145 (Prostate) | 1.4 | 0.15 |

The conjugated oligonucleotide GRN163L had significantly greater telomerase inhibiting activity in vivo than the unconjugated GRN163, as demonstrated in hepatoma cell xenografts (FIG. 1) and flank CAG myeloma tumor xenografts (FIG. 2) following i.v. administration.

Administration of GRN163L inhibited tumor growth in mice (A549-luc IV lung metastases model) for at least 4 weeks after i.v. injection of cancer cells. The dosage was 1 μM biweekly for 5 weeks prior to injection of cancer cells, followed by 5 mg/kg twice weekly after injection. Controls showed substantial tumor growth, but none was apparent in the GRN163L-treated mouse.

IV. Combination Therapy with Gemcitabine and Telomerase Inhibitors

Therapeutic benefits for treatment of cancer can be realized by combining gemcitabine with an oligonucleotide telomerase inhibitor that acts as an hTR template blocking agent. The combination of gemcitabine with the telomerase inhibition may have a supraadditive effect; that is, the combined benefit is greater than would be expected simply from the additive effects of the two therapeutic approaches. This is demonstrated herein for the combination of a telomerase inhibitor and gemcitabine study herein.

In accordance with the present invention, it has been discovered that combined exposure of cancer cells to both gemcitabine and an oligonucleotide telomerase inhibitor enhances the extent to which cell proliferation is inhibited relative to gemcitabine alone, or the telomerase inhibitor alone. The effect is seen both for inhibition of cancer cell growth in vitro, where the inhibition is evidenced by a reduced rate of cell proliferation, and for in vivo treatment of cancer in a mammalian subject, where the inhibition is evidenced by a reduced rate of tumor growth and/or increased survival time of the subject being treated.

In practicing the method of the invention, a subject having a cancer type that is responsive to gemcitabine, or a subject currently receiving cancer therapy with gemcitabine, is initially identified as a candidate for the combined therapy. Preferred cancer indications include, for example, non-small cell lung cancer, pancreatic cancer, breast cancer, oesophageal cancer, and lymphomas, bladder cancer, cancer of the lymph system, epithelial ovarian cancer, cancer of the bile ducts, cancer of the gallbladder, and germ cell tumors of the ovaries and testes.

Thus, an aspect of the invention involves identifying cancer patients who are candidates for effective anti-cancer treatment with a telomerase inhibitor. The candidate patients are those whose cancer is responding to treatment with a gemcitabine, but for whom combined treatment with a telomerase inhibitor is desired to enhance the anti-tumor efficacy of gemcitabine alone.

The cancer should also be one that is responsive to cancer-cell inhibition by telomerase inhibition. As noted above, oligonucleotide telomerase inhibitors, as exemplified by GRN163 and GRN163L, have shown inhibitory activity in vitro against human kidney, lung, pancreatic, brain, colon, prostate, breast, leukemia, lymphoma, myeloma, epidermal, cervical, ovarian and liver cancer cells, and in vivo, via local and systemic delivery, against human brain, prostate, lymphoma, myeloma, cervical, lung, and liver cancer cells. Other preferred targets include small cell lung, esophogeal, head and neck, and stomach cancers.

In the preferred treatment method, the subject is administered gemcitabine, in an amount that is effective inhibiting proliferation of cancer cells in the subject. The dose administered and the dosing schedule will follow, for example, known or recommended doses for gemcitabine employed, as indicated, for example, in the drug product insert or published clinical or animal-model data. One advantage of the present invention is that lower-than-normal doses of gemcitabine may be administered, if necessary, due to the compensating enhancement effect of the telomerase inhibitor. Such a protocol allows for a reduced dosage of gemcitabine, which can have significant toxic effects at higher dosages. Thus, a kit containing a dose of the telomerase inhibitor could optionally contain a product insert having one set of directions for using the inhibitor in monotherapy, and another set of directions for using the inhibitor in a combination therapy with gemcitabine. The set of instructions for the combination therapy could recommend (i) a lower dose of the telomerase inhibitor, when used in combination with gemcitabine, (ii) a lower dose of gemcitabine, when used in combination with the telomerase inhibitor, and/or (iii) a different dosing regimen for one or both inhibitors, when used together, than would normally be recommended for the two agents, when used alone.

The telomerase inhibitor may be administered, before, during, or after administration of gemcitabine. Typically, the two inhibitors are administered in a common dosing regimen, as described below, and the two inhibitors themselves may be administered in a combined-drug composition, e.g., by IV administration, or separately. However, a dosing regimen in which the telomerase inhibitor is administered before or after administering gemcitabine is also contemplated. For example, a person under treatment with a gemcitabine may be subsequently placed on a combined therapy that includes telomerase inhibitor.

Alternatively, the patient may be initially administered gemcitabine, followed one-to-several days later with the telomerase treatment. In this regimen, gemcitabine may function, in part, to sensitize the cancer cells to inhibition by a telomerase inhibition, e.g., by synchronizing the cell-division cycle and/or promoting apoptosis in the cells. Preferred dose levels and dosing schedules are considered further below.

In one exemplary method, gemcitabine is administered in combination with a telomerase-inhibitor oligonucleotide targeted against hTR. FIG. 1 shows the results of the treatment method in which gemcitabine is administered in combination with the telomerase inhibitor GRN163L, for the treatment of A549 tumor cells in a mouse xenograft model. Briefly, A549 cells (approximately $3\times10^{6)}$ were implanted subcutaneously in immunocompromised mice, and treatment with GRN163L and/or gemcitabine was started on days 4, and 14, respectively. Groups of 10 mice each were treated in accordance with one of three protocols: (1) Gemcitabine (100 mg/kg, IP) was administered 2 times/week for the first 1.5 weeks, then once weekly for the remainder of the study. (2) GRN163L (15 mg/kg, IP) was given 3 times/week for the duration of the study. (3) The two agents were administered together according to the individual-agent protocols. After 60 days, tumor mass was assayed by a standard bioluminescence assay, with the results shown in FIG. 1.

As seen, both GRN163L alone, gemcitabine alone, and the two agents together were effective in preventing tumor growth during the treatment period. Greatest reduction in tumor mass was seen with combined treatment.

B. Administration

The therapeutic protocol for administering such combinations will depend on various factors including, but not limited to, the type of cancer, the age and general health of the patient, the aggressiveness of disease progression, the TRF length (terminal restriction fragment length; see Section V below) and telomerase activity of the diseased cells to be treated, and the ability of the patient to tolerate the agents that comprise the combination.

In general, treatment of all carcinoma and hematological malignancy types is contemplated. In selected embodiments, the target disease comprises a solid tumor; in other embodiments, the target disease comprises a hematological malignancy. An exemplary course of treatment involves multiple doses. Sequence of combination treatments will be determined by clinical compliance criteria and/or preclinical or clinical data supporting dose optimization strategies to augment efficacy or reduce toxicity of the combination treatment. In general, various combinations of the telomerase inhibitor and gemcitabine may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. The time between dosages may be for a period from about 1-6 hours, to about 6-12 hours, to about 12-24 hours, to about 1-2 days, to about 1-2 wk or longer following the initiation of treatment. During a course of treatment, the need to complete the planned dosings may be re-evaluated.

The compounds may be administered by direct injection of a tumor or its vasculature. Alternatively, the tumor may be infused or perfused with the therapeutic compounds using any suitable delivery vehicle. The compounds may be administered locally to an affected organ. Systemic administration may also be performed. Continuous administration may be applied where appropriate; for example, where a tumor is excised and the tumor bed is treated to eliminate residual disease. Delivery via syringe or catheterization is preferred. Such continuous perfusion may take place for a period from about 1-6 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs.

The therapeutic agents are administered to a subject, such as a human patient, in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor specific markers such as serum PSA), and improvement in quality of life (as determined by clinical assessment, e.g., Karnofsky score), increased time to progression, disease-free survival and overall survival.

The amount of each agent per dose and the number of doses required to achieve such effects will vary depending on many factors including the disease indication, characteristics of the patient being treated and the mode of administration. Typically, the formulation and route of administration will provide a local concentration at the disease site of between 1 nM and 100 μM of each agent. The physician will be able to vary the amount of the compounds, the carrier, the dosing frequency, and the like, taking into consideration such factors as the particular neoplastic disease state and its severity; the overall condition of the patient; the patient's age, sex, and weight; the mode of administration; the suitability of concurrently administering systemic anti-toxicity agents; monitoring of the patient's vital organ functions; and other factors typically monitored during cancer chemotherapy. In general, the compounds are administered at a concentration that affords effective results without causing excessive harmful or deleterious side effects.

In accordance with the invention, the amount of the agent used in combination with a telomerase inhibitor, especially with respect to gemcitabine, may be less than would be required for the agent used in non-combination therapy.

C. Formulations

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

The liquid carrier for pressurized compositions can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The compositions may be administered topically as a solution, cream, or lotion, by formulation with pharmaceutically acceptable vehicles containing the active compound. The compositions of this invention may be orally administered in any acceptable dosage including, but not limited to, formulations in capsules, tablets, powders or granules, and as suspensions or solutions in water or non-aqueous media. Pharmaceutical compositions and/or formulations comprising the oligonucleotides of the present invention may include carriers, lubricants, diluents, thickeners, flavoring agents, emulsifiers, dispersing aids or binders. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Modes of administration and formulation may be dependent on the drug and its approved mode of administration. For example, IV administration is indicated for gemcitabine. When the telomerase inhibitor is GRN163L, formulation in 0.9% sodium chloride (normal saline) and administration by IV is a preferred route, preferably via infusion over 4-8 hours, e.g. a 6 hr infusion.

While the lipid-conjugated oligonucleotides described herein, such as GRN163L, have superior characteristics for cellular and tissue penetration, these and other compounds may be formulated to provide further benefit in this area, e.g. in liposome carriers. The use of liposomes to facilitate cellular uptake is described, for example, in U.S. Pat. Nos. 4,897,355 and 4,394,448, and numerous publications describe the formulation and preparation of liposomes. Liposomal formulations can also be engineered, by attachment of targeting ligands to the liposomal surface, to target sites of neovascularization, such as tumor angiogenic regions. The compounds can also be formulated with additional penetration/transport enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Other useful adjuvants include substrates for transendothelial migration, such as glucose uptake systems for facilitated egress from the vascular space to the tumor microenvironment.

V. Measurement of Telomere Length, Telomerase Activity, and/or Cell Proliferation When employing a therapeutic regimen that involves administration of a telomerase inhibitor, it may be useful to determine telomere length and/or telomerase activity in a cell or tissue sample. These parameters can be measured by assays known in the art. Telomere length can be measured by a flow cytometry method using fluorescence in situ hybridization, referred to as flow FISH (see e.g. M. Hultdin et al., *Nucleic Acids Res.* 26(16):3651-6, 1998; N. Rufer et al., *Nature Biotechnology* 16:743-7, 1998). Other methods include terminal restriction fragment (TRF) analysis, in which genomic DNA is digested with a restriction enzyme having a four-base recognition sequence not present in telomere repeat sequences, and the restriction fragments are separated according to size, e.g. by gel electrophoresis. See, for example, U.S. Pat. No. 5,489,508 (West et al.) and Harley et al., *Nature* 345:458, 1990. The West et al. patent also describes methods of measuring telomere length by an "anchored terminal primer" method and by a modified Maxam-Gilbert reaction.

In addition, a more rapid response to a telomerase inhibiting agent may be predicted for tumor cells having shorter telomeric DNA, although telomerase has been shown to have other inhibitory effects independent of telomere length. (e.g. Stewart et al., *PNAS* 99:12606, 2002; Zhu et al., *PNAS* 93:6091, 1996; Rubaiyat et al., *Oncogene* 24(8):1320, 2005); and Folini et al., *Curr. Pharm. Design* 11(9):1105, 2005).

The TRAP assay (see Experimental, below) is a standard method for measuring telomerase activity in a cell extract system (Kim et al., *Science* 266:2011, 1997; Weinrich et al., *Nature Genetics* 17:498, 1997). Briefly, this assay measures the amount of nucleotides incorporated into elongation products (polynucleotides) formed by nucleotide addition to a labeled telomerase substrate or primer. The TRAP assay is described in detail in U.S. Pat. Nos. 5,629,154, 5,837,453 and 5,863,726, and its use in testing the activity of telomerase inhibitory compounds is described in various publications, including WO 01/18015. In addition, the following kits are available commercially for research purposes for measuring telomerase activity: TRAPeze™XK Telomerase Detection Kit (Intergen Co., Purchase N.Y.); and TeloTAGGG Telomerase PCR ELISA plus (Roche Diagnostics, Indianapolis Ind.).

The anticancer activity of the therapeutic combinations can be evaluated using standard in vitro and in vivo assays. The ability of a composition to specifically inhibit the growth of tumor cells can be assayed using tumor cell lines in vitro, or in xenograft animal models in vivo. A preferred protocol for such growth curve assays is the short term cell viability assay described in Asai et al. (2003, cited above). In established xenograft models of human tumors, the test compound is administered either directly to the tumor site or systemically, and the growth of the tumor is followed by physical measurement. A preferred example of a suitable in vivo tumor xenograft assay is also described in Asai et al. (2003, cited above). Other examples are described in Scorski et al., *Proc. Natl. Acad. Sci. USA,* 94: 3966-3971 (1997) and Damm et al., *EMBO J.,* 20:6958-6968 (2001).

Experimental

A. Preparation and Lipid Conjugation of Oligonucleotide N3'→P5' Phosphoramidates or N3'→P5' Thiophosphoramidates These compounds may be prepared as described, for example, in McCurdy et al., *Tetrahedron Letters* 38:207-210 (1997) or Pongracz & Gryaznov, *Tetrahedron Letters* 49:7661-7664 (1999). The starting 3'-amino nucleoside monomers may be prepared as described in Nelson et al., *J. Org. Chem.* 62:7278-7287 (1997) or by the methods described in Gryaznov et al., US Appn. Pubn. No. 2006/0009636.

A variety of synthetic approaches can be used to conjugate a lipid moiety L to the oligonucleotide, depending on the nature of the linkage selected; see, for example, Mishra et al., *Biochim. et Biophys. Acta* 1264:229-237 (1995), Shea et al., *Nucleic Acids Res.* 18:3777-3783 (1995), or Rump et al., *Bioconj. Chem.* 9:341-349 (1995). Typically, conjugation is achieved through the use of a suitable functional groups at an oligonucleotide terminus. For example, the 3'-amino group present at the 3'-terminus of the NP and NPS oligonucleotides can be reacted with carboxylic acids, acid chlorides, anhydrides and active esters, using suitable coupling catalysts, to form an amide linkage. Thiol groups are also suitable as functional groups (see Kupihar et al., *Bioorg. Med. Chem.* 9:1241-1247 (2001)). Various amino- and thiol-functionalized modifiers of different chain lengths are commercially available for oligonucleotide synthesis.

Specific approaches for attaching lipid groups to a terminus of an NP or NPS oligonucleotide include those described in US Appn. Pubn. No. 2005/0113325, which is incorporated herein by reference. In addition to the amide linkages noted above, for example, lipids may also be attached to the oligonucleotide chain using a phosphoramidite derivative of the lipid, to produce a phosphoramidate or thiophosphoramidate linkage connecting the lipid and the oligonucleotide. The free 3'-amino group of the fully protected support-bound oligonucleotide may also be reacted with a suitable lipid aldehyde, followed by reduction with sodium cyanoborohydride, which produces an amine linkage.

For attachment of a lipid to the 5' terminus, as also described in US Appn. Pubn. No. 2005/0113325, the oligonucleotide can be synthesized using a modified, lipid-containing solid support. Reaction of 3-amino-1,2-propanediol with a fatty acyl chloride (RC(O)Cl), followed by dimethoxytritylation of the primary alcohol and succinylation of the secondary alcohol, provides an intermediate which is then coupled, via the free succinyl carboxyl group, to the solid support. An example of a modified support is shown below, where S— represents a long chain alkyl amine CPG support, and R represents a lipid.

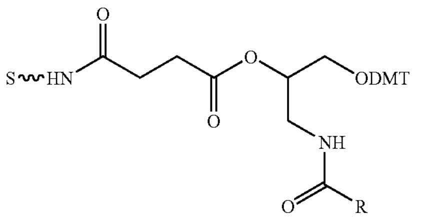

This procedure is followed by synthesis of the oligonucleotide in the 5' to 3' direction, as described, for example, in Pongracz & Gryaznov (1999), starting with deprotection and phosphitylation of the -ODMT group. This is effective to produce, for example, the following structure, after cleavage from the solid support:

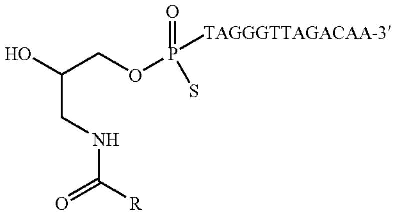

The structure above, when —R is —$(CH_2)_{13}CH_3$ (palmitoyl), is designated herein as GRN163L.

B. FlashPlate™ Assay

This assay was carried out essentially as described in Asai et al., Cancer Research, 63:3931 3939 (2003). Briefly, the assay detects and/or measures telomerase activity by measuring the addition of TTAGGG telomeric repeats to a biotinylated telomerase substrate primer. The biotinylated products are captured on streptavidin-coated microtiter plates, and an oligonucleotide probe complementary to 3.5 telomere repeats, labeled with 33P, is used for measuring telomerase products. Unbound probe is removed by washing, and the amount of probe annealing to the captured telomerase products is determined by scintillation counting.

C. TRAP Assay

The ability of a compound to increase or inhibit telomerase activity in a cell can be determined using the TRAP (Telomeric Repeat Amplification Protocol) assay, which is described, for example, in Kim et al., U.S. Pat. No. 5,629,154; Harley et al., U.S. Pat. No. 5,891,639; and Harley et al., PCT Pubn. No. WO 2005/000245. Briefly, telomerase-expressing tumor cell lines are incubated with test compositions, lysed, and treated with a labeled oligonucleotide telomerase substrate, appropriate primers, and internal standard for quantitation purposes. Depending on the telomerase activity of the medium, telomere repeats will be added to the substrate, to form telomerase extended products. The mixture is incubated at room temperature, followed by multiple cycles of PCR. The mixture is separated on a gel, and labeled extension product is detected and quantitated via comparison with the internal standard.

Although the invention has been described with respect to specific agents, formulations, and applications, it will be appreciated that various modifications may be made without departing from the invention as claimed.

Sequence Listing

SEQ ID NO: 1: the RNA component of human telomerase (hTR):

```
GGGUUGCGGA GGGUGGGCCU GGGAGGGGUG GUGGCCAUUU UUUGUCUAAC CCUAACUGAG   60

AAGGGCGUAG GCGCCGUGCU UUUGCUCCCC GCGCGCUGUU UUUCUCGCUG ACUUUCAGCG  120

GGCGGAAAAG CCUCGGCCUG CCGCCUUCCA CCGUUCAUUC UAGAGCAAAC AAAAAAUGUC  180

AGCUGCUGGC CCGUUCGCCU CCCGGGGACC UGCGGCGGGU CGCCUGCCCA GCCCCCGAAC  240

CCCGCCUGGA GCCGCGGUCG GCCCGGGGCU UCUCCGGAGG CACCCACUGC CACCGCGAAG  300

AGUUGGGCUC UGUCAGCCGC GGGUCUCUCG GGGGCGAGGG CGAGGUUCAC CGUUUCAGGC  360

CGCAGGAAGA GGAACGGAGC GAGUCCCGCC GCGGCGCGAU UCCCUGAGCU GUGGGACGUG  420

CACCCAGGAC UCGGCUCACA CAUGCAGUUC GCUUUCCUGU UGGUGGGGGG AACGCCGAUC  480

GUGCGCAUCC GUCACCCCUC GCCGGCAGUG GGGGCUUGUG AACCCCCAAA CCUGACUGAC  540

UGGGCCAGUG UGCU
```

| SEQ ID NOS: 2-26, the nucleotide sequences of targeting agents against SEQ ID NO: 1: | |
|---|---|
| ACATTTTTTGTTTGCTCTAG | 2 |
| GCTCTAGAATGAACGGTGGAAGGCGGCAGG | 3 |
| GTGGAGGCGGCAGG | 4 |
| GGAAGGCGGCAGG | 5 |
| GTGGAAGGCGGCA | 6 |
| GTGGAAGGCGG | 7 |
| CGGTGGAAGGCGG | 8 |
| ACGGTGGAAGGCG | 9 |
| AACGGTGGAAGGCGGC | 10 |
| ATGAACGGTGGAAGGCGG | 11 |
| TAGGGTTAGACAA | 12 |
| CAGTTAGGGTTAG | 13 |
| TAGGGTTAGACA | 14 |
| TAGGGTTAGAC | 15 |
| GTTAGGGTTAG | 16 |
| GTTAGGGTTAGAC | 17 |
| GTTAGGGTTAGACAA | 18 |
| GGGTTAGAC | 19 |
| CAGTTAGGG | 20 |
| CCCTTCTCAGTT | 21 |
| CGCCCTTCTCAG | 22 |
| TAGGTGTAAGCAA | 23 |
| TTGTCTAACCCTA | 24 |
| GTTGAGTGTAG | 25 |
| TTAGGG | 26 |
| TTTTTTTTTT | 27 |

It is claimed:

1. A method for inhibiting the proliferation of cancer cells, comprising (a) exposing the cells to gemcitabine, and (b) either proceeding, following, or concomitantly with step (a), exposing the cells to a telomerase inhibitor consisting of an oligonucleotide 10-20 bases in length which is characterized by:

(i) N3'→P5' thiophosphoramidate linkages;

(ii) having the sequence identified as SEQ ID NO:12;

(iii) a palmitoyl (C16) moiety linked to the 5' terminus of the oligonucleotide via a glycerol or aminoglycerol linker.

2. The method of claim 1, wherein the oligonucleotide is the compound designated herein as GRN163L.

3. The method of claim 1, wherein the telomerase inhibitor is the compound designated herein as GRN163L, and step (b) includes infusing the telomerase inhibitor intravenously to the subject under infusion conditions effective to produce a blood concentration of the inhibitor of between 1 nM and 100 μM.

4. The method of claim 1, wherein each exposing step (a) and (b) includes administering gemcitabine and the telomerase inhibitor to the subject in an amount effective, when each agent is administered alone, to inhibit proliferation of cancer cells in the subject.

5. The method of claim 1, wherein the telomerase inhibitor and gemcitabine are administered to a subject diagnosed with a cancer selected from the group consisting of non-small cell lung cancer, pancreatic cancer, breast cancer, oesophageal cancer, and lymphomas, bladder cancer, cancer of the lymph system, epithelial ovarian cancer, cancer of the bile ducts, cancer of the gallbladder, and germ cell tumors of the ovaries and testes.

6. The method of claim 1, wherein said method provides a supraadditive inhibiting effect relative to the effects of the individual gemcitabine and the telomerase inhibitor agents.

7. A method for enhancing the anti-cancer treatment efficacy of gemcitabine administered to a subject, comprising administering to the subject, before, during, or after administering gemcitabine, an oligonucleotide telomerase inhibitor consisting of an oligonucleotide 10-20 bases in length which is characterized by:

(iv) N3'→P5' thiophosphoramidate linkages;

(v) having the sequence identified as SEQ ID NO:12;

(vi) a palmitoyl (C16) moiety linked to the 5' terminus of the oligonucleotide via a glycerol or aminoglycerol linker.

8. The method of claim 7, wherein the telomerase inhibitor is administered in an amount effective to inhibit the proliferation of cancer cells in the subject, when the telomerase inhibitor is administered alone.

9. The method of claim 7, wherein enhanced treatment efficacy is evidenced by an increased survival time of the subject, an inhibition of tumor growth in the subject, or a combination thereof.

10. The method of claim 7, wherein the telomerase inhibitor is the compound designated herein as GRN163L.

11. The method of claim 7, wherein the telomerase inhibitor and gemcitabine are administered to the subject as a composition containing both inhibitors.

* * * * *